United States Patent
Taki et al.

(10) Patent No.: US 12,280,220 B2
(45) Date of Patent: Apr. 22, 2025

(54) SLEEP APNEA TREATMENT APPARATUS AND METHOD

(71) Applicant: MaRI Co., Ltd., Kyoto (JP)

(72) Inventors: Hirofumi Taki, Kyoto (JP); Yoshiaki Motoyama, Kyoto (JP); Shigeaki Okumura, Kyoto (JP)

(73) Assignee: MaRI Co., Ltd., Kyoto (JP)

( * ) Notice: Subject to any disclaimer, the term of this patent is extended or adjusted under 35 U.S.C. 154(b) by 1001 days.

(21) Appl. No.: 17/297,799

(22) PCT Filed: Nov. 29, 2019

(86) PCT No.: PCT/IB2019/001283
§ 371 (c)(1),
(2) Date: May 27, 2021

(87) PCT Pub. No.: WO2020/109863
PCT Pub. Date: Jun. 4, 2020

(65) Prior Publication Data
US 2022/0047839 A1    Feb. 17, 2022

Related U.S. Application Data

(60) Provisional application No. 62/925,104, filed on Oct. 23, 2019, provisional application No. 62/847,742, (Continued)

(51) Int. Cl.
*A61M 21/02* (2006.01)
*A61B 5/00* (2006.01)
(Continued)

(52) U.S. Cl.
CPC ............ *A61M 21/02* (2013.01); *G16H 20/40* (2018.01); *G16H 40/63* (2018.01); (Continued)

(58) Field of Classification Search
CPC .................................................. A61B 5/4818
See application file for complete search history.

(56) References Cited

U.S. PATENT DOCUMENTS

| 2,193,399 A | 3/1940 | Fisher |
| 5,313,525 A | 5/1994 | Klasco |

(Continued)

FOREIGN PATENT DOCUMENTS

| FR | 564 750 | 1/1924 |
| JP | 2011-519288 A | 7/2011 |

(Continued)

OTHER PUBLICATIONS

Communication pursuant to Rules 161(1) and 162 EPC issued Jul. 7, 2021 in European Patent Application No. 19853255.8, 3 pages.

(Continued)

*Primary Examiner* — Thaddeus B Cox
(74) *Attorney, Agent, or Firm* — McBee Moore & Vanik IP, LLC

(57) ABSTRACT

A sleep apnea treatment apparatus including a stimulation device that applies a stimulation to a subject, and a controller including circuitry which receives sounds produced by the subject, converts the sounds to received sound signals, obtains snoring sound information from the received sound signals, calculates an impact of snoring sound produced by the subject based on the snoring sound information, and causes the stimulation device to apply the stimulation to the subject when the impact is higher than a threshold.

14 Claims, 17 Drawing Sheets

Related U.S. Application Data filed on May 14, 2019, provisional application No. 62/774,085, filed on Nov. 30, 2018.

(51) Int. Cl.
 G16H 20/40 (2018.01)
 G16H 40/63 (2018.01)
 H04R 1/28 (2006.01)
 A61M 21/00 (2006.01)

(52) U.S. Cl.
 CPC ......... H04R 1/2811 (2013.01); H04R 1/2865 (2013.01); *A61B 5/4818* (2013.01); *A61M 2021/0022* (2013.01); *A61M 2021/0033* (2013.01); *A61M 2021/0083* (2013.01); *A61M 2205/3317* (2013.01); *A61M 2205/3375* (2013.01); *A61M 2230/06* (2013.01); *A61M 2230/205* (2013.01); *A61M 2230/40* (2013.01)

(56) References Cited

U.S. PATENT DOCUMENTS

| | | | |
|---|---|---|---|
| 5,444,786 | A | 8/1995 | Raviv |
| 5,664,020 | A | 9/1997 | Goldfarb et al. |
| 2004/0173402 | A1 | 9/2004 | Morkerken |
| 2012/0172730 | A1* | 7/2012 | Delos ............... A61B 5/4818 600/484 |
| 2014/0194793 | A1 | 7/2014 | Nakata et al. |
| 2015/0087894 | A1* | 3/2015 | Rink ................ A61B 5/4812 600/27 |
| 2016/0022204 | A1 | 1/2016 | Mostov |
| 2019/0159960 | A1 | 5/2019 | Nakata et al. |
| 2020/0160828 | A1 | 5/2020 | Taki et al. |

FOREIGN PATENT DOCUMENTS

| | | | |
|---|---|---|---|
| JP | 2011145111 | A * | 7/2011 |
| JP | 2016-515904 | A | 6/2016 |
| JP | 2017506920 | A | 3/2017 |
| JP | 2017523820 | A | 8/2017 |
| WO | WO 96/31083 | A1 | 10/1996 |
| WO | WO 2009/124297 | A1 | 10/2009 |
| WO | WO 2014/165834 | A1 | 10/2014 |
| WO | 2015107710 | A1 | 7/2015 |
| WO | WO 2018/215836 | A1 | 11/2018 |

OTHER PUBLICATIONS

Javaid, AQ, et al., "Towards Detection of Sleep Apnea Events by Combining Different Non-Contact Measurement Modalities", 38th Annual International Conference of the IEEE Engineering in Medicine and Biology Society (EMBC), pp. 5307-5310, 2016. doi: 10.1109/EMBC.2016.7591925.

International Search Report and Written Opinion issued on Jul. 24, 2020 in PCT/IB2019/001283 filed on Nov. 29, 2019.

"Apnea-hypopnea index—Wikipedia," Wikipedia, Retrieved from the Internet: https://en.wikipedia.org/w/index.php?title=Apnea-hypopnea index&oldid=860897222, Sep. 23, 2018, Retrieved on Apr. 14, 2020, 1 total page, XP055685183.

Japanese Office Action issued on Jul. 25, 2023 in Japanese Patent Application No. 2021-530923 (with English translation), 10 pages.

* cited by examiner

SLEEP APNEA TREATMENT APPARATUS AND METHOD

CROSS-REFERENCE TO RELATED APPLICATIONS

The present application is based upon and claims the benefits of priority to U.S. Provisional Application No. 62/774,085, filed Nov. 30, 2018, and U.S. Provisional Application No. 62/847,742, filed May 14, 2019, and U.S. Provisional Application No. 62/925,104, filed Oct. 23, 2019. The entire contents of all of the above applications are incorporated herein by reference.

TECHNICAL FIELD

The present invention is directed to a sleep apnea treatment apparatus and sleep apnea treatment method that radiate low-frequency sound to a subject in order to treat sleep apnea and to alleviate the symptoms of sleep apnea.

BACKGROUND ART

Snoring is a prevalent disorder among general population. The prevalence of chronic snoring is estimated to be 40% in adult men and 20% in adult women (NPL 1). The snoring sound is determined by many factors (NPL 2): including the route of breathing (NPL 3), the predominant sites of upper airway narrowing (NPL 4), and sleep stage and body position (NPL 5).

Snoring is one of the important manifestations for obstructive sleep apnea (OSA) that causes medical morbidity and mortality (NPL 6). Obstructive sleep apnea is a sleep disorder in which breathing is repeatedly interrupted during sleep (NPL 7). Sleep apnea causes not only sleeplessness but also the increased incidence of various diseases and symptoms, e.g. high blood pressure, heart attack, cardiac arrhythmia, stroke and depression. Continuous positive airway pressure (CPAP) is the most common treatment for obstructive sleep apnea (NPL 8). However, patients with obstructive sleep apnea feel frustrations because of several problems of CPAP (NPL 9). Therefore, most inventors focus on OSA treatments (PL 1, PL 2, PL 3, NPL 10). However, these treatments require behavior change or invasive procedure.

Snoring sound is also a large problem for the bed partner of a snorer. There are many attempts that suppress the impact of snoring sound. Ear plug is a most common solution to suppress the impact of snoring noise. However, ear plug also suppress important sounds, e.g. the sound of alert system. In addition, the attachment of ear plug requires a behavior change. Noise cancelling system is an attempt that cancels snoring sound (PL 4); however, it requires a behavior change and it is impossible to suppress the snoring sound effectively. Another strategy employs a system with an eye cover that radiates flash light when snoring sound intensity exceeds a predetermined threshold (PL 5). The invention tried to avoid affecting user's normal sleep; however, the attachment of an eye cover to a user requires a behavior change. Anti-snoring bed system (PL 6) attempts to stop snoring by changing the configuration of the bed. This system assumes the use of a special bed, that is, it is not applicable to subjects that use normal beds.

CITATION LIST PATENT LITERATURE

PL 1 T. R. Shantha, "Device for snoring and obstructive sleep apnea treatment," U.S. Pat. No. 9,072,613B2.
PL 2 F. Li, Z. Li, "Method and device for intelligently stopping snoring," WO2015027744A1.
PL 3 W. Li, "Anti-snoring device," U.S. Pat. No. 9,554,938 B2.
PL 4 G. Raviv, "Snoring suppression system," U.S. Pat. No. 5,444,786A.
PL 5 H. Bruckhoff, "Device for snoring prevention," EP0493719A1.
PL 6 H.-D. Lin, "Automated anti-snoring bed system," U.S. Pat. No. 8,418,289B2.

CITATION LIST NON PATENT LITERATURE

NPL 1 V. Hoffstein, "Apnea and snoring: state of the art and future directions," Acta Otorhinolaryngol Belg 2002; 56(2):205-36.
NPL 2 D. Pevernagie, R. M. Aarts, M. De Meyer, "The acoustics of snoring," Sleep Med Rev. 2010 April; 14(2): 131-44.
NPL 3 Liistro G, Stanescu D, Veriter C. Pattern of simulated snoring is different through mouth and nose. J Appl Physiol 1991; 70(6):2736-41.
NPL 4 S. J. Quinn, N. Daly, P. D. Ellis, "Observation of the mechanism of snoring using sleep nasendoscopy," Clin Otolaryngol 1995; 20(4):360-4.
NPL 5 H. Nakano, T. Ikeda, M. Hayashi, E. Ohshima, A. Onizuka, "Effects of body position on snoring in apneic and nonapneic snorers," Sleep 2003; 26(2):169-72.
NPL 6 N. M. Punjabi, "The Epidemiology of Adult Obstructive Sleep Apnea," Proc Am Thorac Soc. 2008 Feb. 15; 5(2):136-43.
NPL 7 www.sleepfoundation.org/sleep-apnea
NPL 8 www.sleepfoundation.org/excessive-sleepiness-osa/treatments/cpap-treatment
NPL 9 www.mayoclinic.org/diseases-conditions/sleep-apnea/in-depth/cpap/art-20044164
NPL 10 www.sleepreviewmag.com/2014/09/alternative-therapies-obstructive-sleep-apnea/

SUMMARY OF THE INVENTION

According to an aspect of the present invention, a sleep apnea treatment apparatus includes a stimulation device that applies a stimulation to a subject, and a controller including circuitry which receives sounds produced by the subject, converts the sounds to received sound signals, obtains snoring sound information from the received sound signals, calculates an impact of snoring sound produced by the subject based on the snoring sound information, and causes the stimulation device to apply the stimulation to the subject when the impact is higher than a threshold.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF EMBODIMENTS

Figure 1:
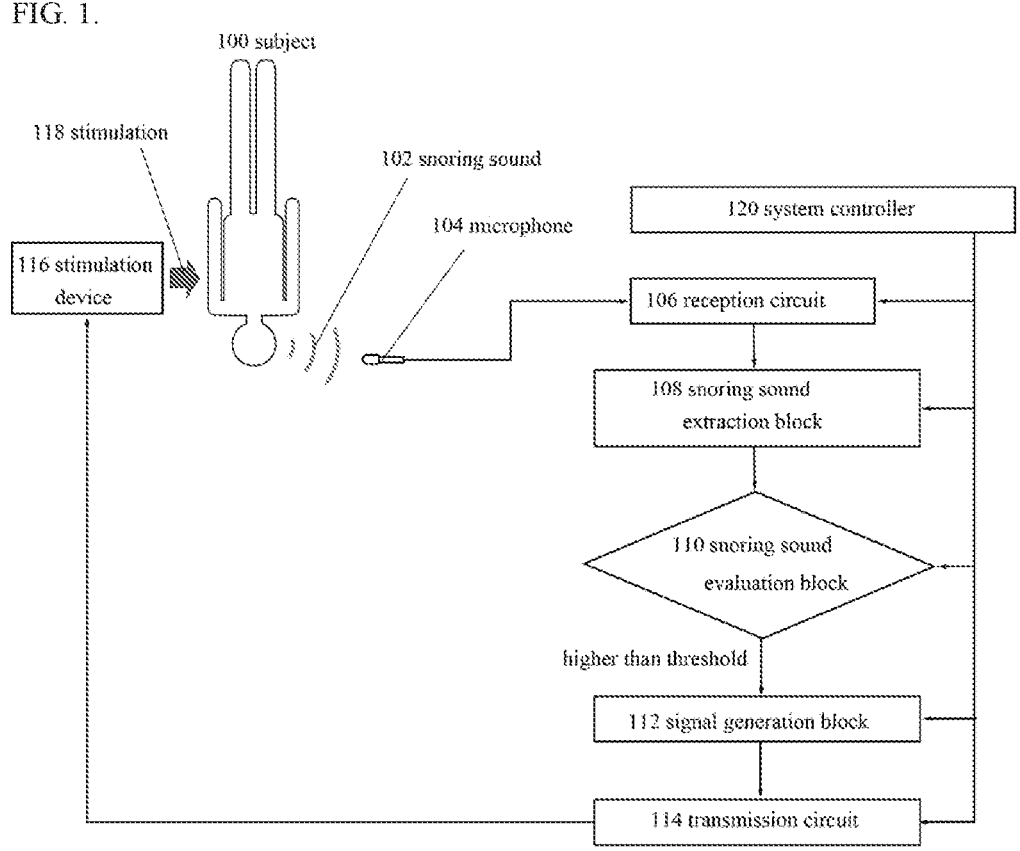
FIG. 1 is a schematic diagram of a sleep apnea treatment apparatus according to an embodiment of the present invention.

The embodiments will now be described with reference to the accompanying drawings, wherein like reference numerals designate corresponding or identical elements throughout the various drawings.

CPAP is an important treatment for obstructive sleep apnea, however, wearing a CPAP device and forced air cause frustration to patients who use CPAP. Snoring sound is also a large problem for the bed partner of a snorer.

In one aspect, the present invention aims at the application of stimulation to a subject in order to stop or alleviate apnea, hypopnea, and/or snoring of a subject during sleep. The sleep apnea treatment apparatus according to an embodiment of the present invention is an apparatus that radiates low-frequency sound to a subject when a subject becomes apnea, hypopnea and/or precursor condition of apnea and hypopnea during sleep, including: a low-frequency sound generator with a transmission circuit that radiates low-frequency sound to a subject; and a controller including circuitry which converts a plurality of sounds produced by a subject to received signals, obtains breathing information from received signals, processes the breathing information such that an index corresponding to breathing interruption, hypopnea, snoring, and/or precursor condition of apnea and hypopnea is determined based on the breathing information, and causes the low-frequency sound generator to apply the low-frequency sound to the subject when the index is higher than a threshold.

Another aspect of the present invention is a sleep apnea treatment method including: converting sounds produced by a subject to received signals; obtaining breathing information from received signals; processing the breathing information such that an index corresponding to breathing interruption, hypopnea, snoring, and/or precursor condition of apnea and hypopnea is determined based on the breathing information; and applying the low-frequency sound to the subject when the index is higher than a threshold.

A sleep apnea treatment apparatus according to one embodiment of the present invention includes an apparatus that applies stimulation 118 to a subject 100 when a subject snores. FIG. 1 shows a schematic diagram of a sleep apnea treatment apparatus employing an embodiment of the present invention. The apparatus is provided with one or plural microphones 104 with one or plural reception circuits 106 that detect and receive sounds produced by a subject 100 and convert a plurality of sounds produced by a subject 100 to a plurality of received signals; a snoring sound extraction block 108 that extracts snoring sound information from a plurality of received signals; a snoring sound evaluation block 110 that evaluates snoring sound information and detects snoring; a signal generation block 112 that generates signals in order to produce stimulation 118 applied to a subject 100 using a stimulation device 116; and a stimulation device 116 with a transmission circuit 114 that applies stimulation 118 to a subject 100. A system controller 120 controls these operations of the sleep apnea treatment apparatus. The system controller 120 determines/calculates an impact of snoring sound produced by the subject based on the snoring sound information, compares the impact with a predetermined threshold which may be stored in a memory, and causes the stimulation device 116 to apply the stimulation 118 to the subject 100 when the impact is determined as higher than the threshold. Impact is estimated by the intensity of the received sound signal. The threshold is determined by the intensity of the received sound signals. For example, the threshold may be set to the average intensity of the received sound signals when the subject snores.

A sleep apnea treatment apparatus may stimulate a subject when a subject becomes apnea during sleep. The apparatus is provided with one or plural microphones 104 with one or plural reception circuits 106 that receive sounds produced by a subject 100 and convert a plurality of sounds produced by a subject 100 to a plurality of received signals; a sleep information extraction block 200 that extracts breathing information from a plurality of received signals; a sleep apnea evaluation block 202 that evaluates breathing information and detects breathing interruption, snoring, and/or hypopnea of a subject; a signal generation block 112 that generates signals in order to produce stimulation 118 applied to a subject 100 using a stimulation device 116; and a stimulation device 116 with a transmission circuit 114 that applies stimulation 118 to a subject 100. The system controller 120 controls these operations of the sleep apnea treatment apparatus. The system controller 120 determines/calculates an index corresponding to breathing interruption, hypopnea, and/or precursor condition of apnea and hypopnea based on the breathing information, compares the index with a predetermined threshold which may be stored in a memory, and cause the stimulation device 116 to apply the stimulation 118 to the subject 100 when the index is higher than a threshold.

In embodiments of the present invention, a system controller 120 may be implemented by at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read.

In embodiments of the present invention, a system controller 120 may be a computer that includes central processing unit (CPU) and a memory such as read-only memory (ROM) and random access memory (RAM). The CPU of the controller can be a single-core processor (which includes a single processing unit) or a multi-core processor. The computer may be a mobile device such as a personal digital assistant (PDA), laptop computer, field-programmable gate array, or cellular telephone.

Figure 2:
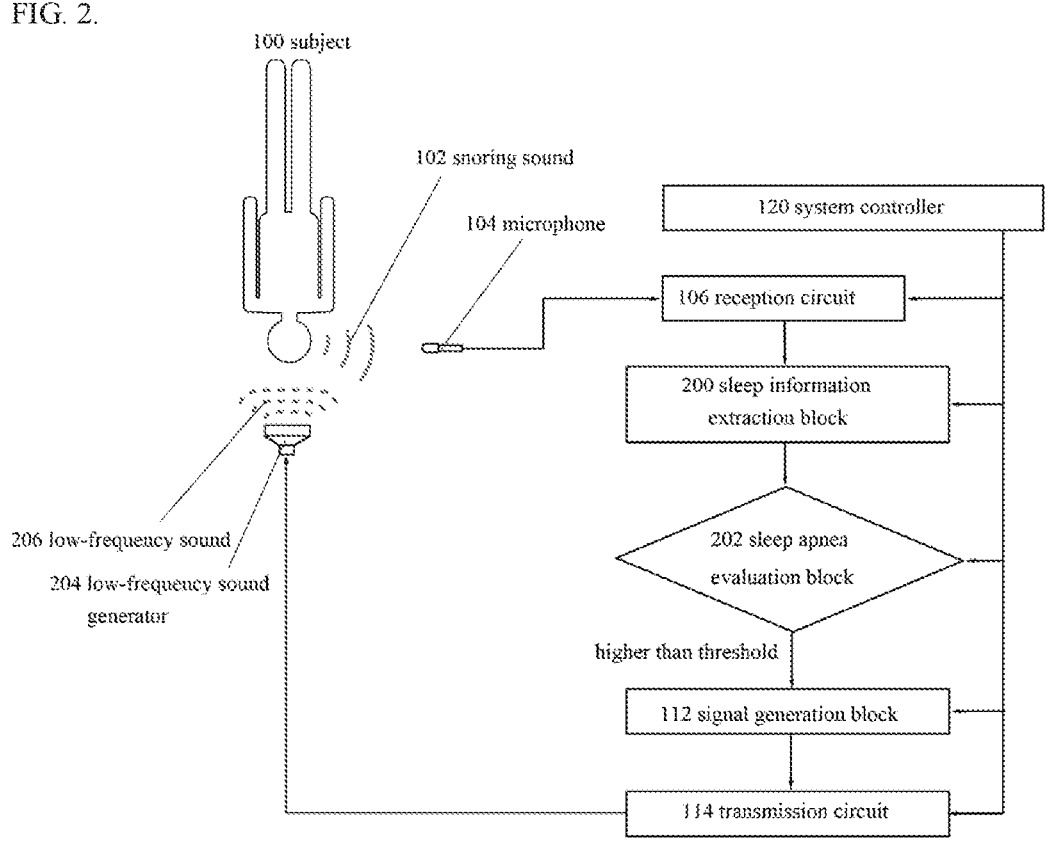
FIG. 2 is a schematic diagram of a sleep apnea treatment apparatus including a low-frequency sound generator.

A sleep apnea treatment apparatus may radiate low-frequency sound to a subject when a subject becomes apnea during sleep. FIG. 2 shows a schematic diagram of a sleep apnea treatment apparatus employing an embodiment of the present invention. The apparatus is provided with one or plural microphones 104 with one or plural reception circuits 106 that convert a plurality of sounds produced by a subject to a plurality of received signals; a sleep information extraction block 200 that extracts breathing information from a plurality of received signals; a sleep apnea evaluation block 202 that evaluates breathing information and detects breathing interruption, hypopnea, snoring, and/or precursor condition of apnea and hypopnea of a subject; a signal generation block 112 that generates signals in order to produce low-frequency sound 206 using a low-frequency sound generator 204; and a low-frequency sound generator 204 with a transmission circuit 114 that radiates low-frequency sound 206 to a subject 100.

Figure 3:
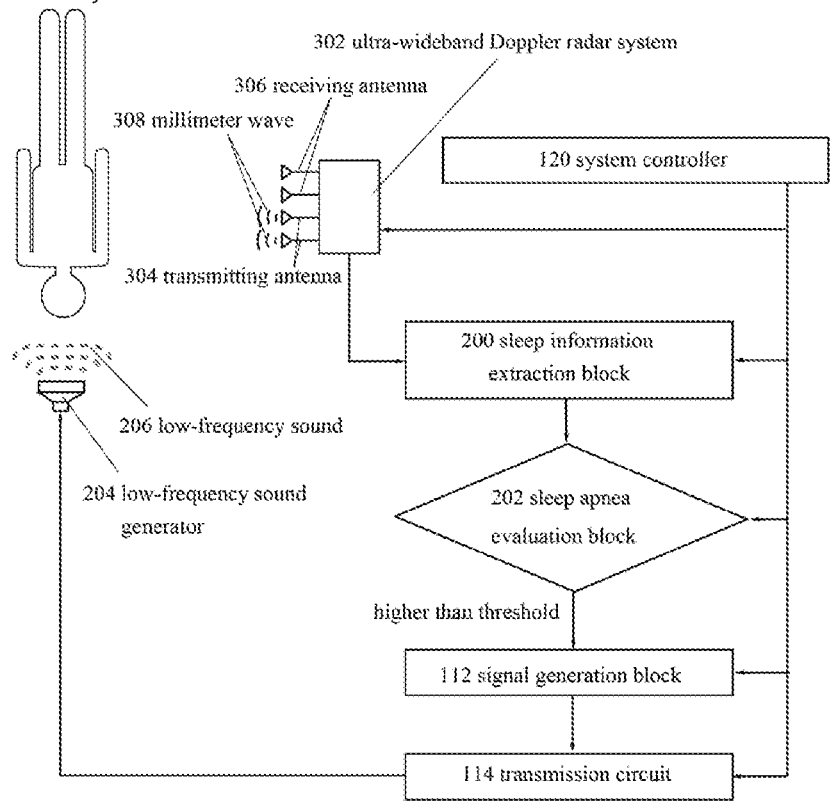
FIG. 3 is a schematic diagram of a sleep apnea treatment apparatus that radiates low-frequency sound to a subject when a subject becomes apnea during sleep, where an ultra-wideband Doppler radar system is employed to acquire breathing information.

A sleep apnea treatment apparatus may employ an ultra-wideband Doppler radar system in order to obtain breathing information. FIG. 3 shows a schematic diagram of a sleep apnea treatment apparatus employing an embodiment of the present invention. An ultra-wideband Doppler radar system 302 includes one or plural transmitting antennas 304 and one or plural receiving antennas 306. Millimeter waves 308 are transmitted from plural transmitting antennas 304. Transmitted millimeter waves 308 can be modulated using one of pulse compression techniques, e.g. m-sequence. Transmitted millimeter waves 308 are reflected at the body surface of a subject 100. Reflected millimeter waves are received by plural receiving antennas 306. Two transmitting antennas 304 and two receiving antennas 306 results in 2×2=4 channels. This system is called a multiple-input multiple-output (MIMO) system. Plural ultra-wideband Doppler radar systems results in the increase of channels because in general the number of channels is equal to the multiplication of the number of transmitting antennas and the number of receiving antennas. A sleep information extraction block 200 extracts breathing information from a plurality of received signals, that is the information of channels, acquired by an ultra-wideband Doppler radar system. Breathing information includes respiration rate. A sleep information extraction block 200 may extract heartbeat information, heart rate, and body position of a subject. A sleep apnea evaluation block 202 detects breathing interruption, that is apnea, of a subject. When a sleep apnea evaluation block 202 detects apnea of a subject, a signal generation block 112 generates signals to produce low-frequency sound 206 using a low-frequency sound generator 204. A low-frequency sound generator 204 with a transmission circuit 114 radiates low-frequency sound to a subject 100 in order to stop or alleviate apnea by the stimulation of the low-frequency sound radiation.

Figure 4:
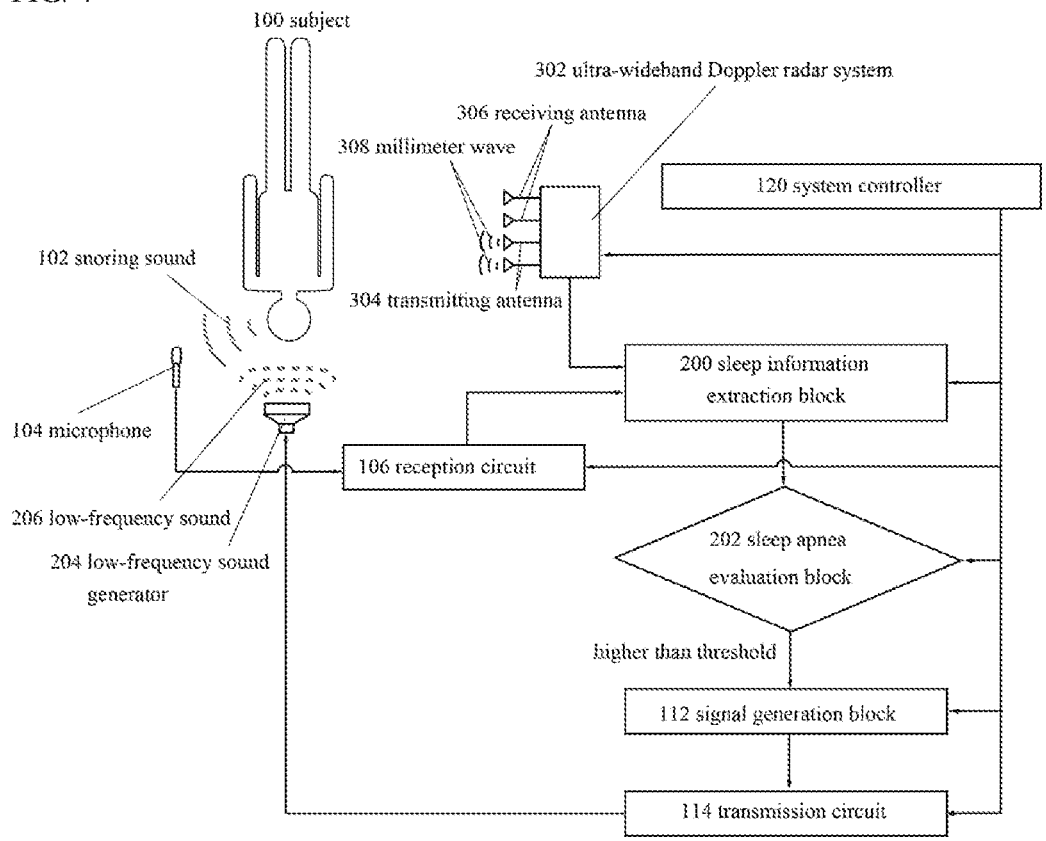
FIG. 4 is a schematic diagram of a sleep apnea treatment apparatus that radiates low-frequency sound to a subject when a subject becomes apnea or snores during sleep, where an ultra-wideband Doppler radar system and a microphone are employed to acquire breathing information.

A sleep apnea treatment apparatus may employ an ultra-wideband Doppler radar system 302 and a microphone 104 with reception circuit 106 in order to obtain breathing information. FIG. 4 shows a schematic diagram of a sleep apnea treatment apparatus employing an embodiment of the present invention. A microphone 104 with a reception circuit 106 converts a plurality of sounds produced by a subject to a plurality of received sound signals. A microphone 104 with a reception circuit 106 in a cell phone is also applicable for the acquisition of a plurality of received sound signals. A sleep information extraction block 200 extracts snoring sound information from a plurality of received sound signals acquired by a microphone 104 with a reception circuit 106 and breathing information from a plurality of received signals acquired by an ultra-wideband Doppler radar system 302. A sleep apnea evaluation block 202 detects breathing interruption and snoring of a subject. A sleep apnea evaluation block 202 may detect hypopnea of a subject. When a sleep apnea evaluation block 202 detects breathing interruption or snoring of a subject, a signal generation block 112 generates signals to produce low-frequency sound 206 using a low-frequency sound generator 204. A low-frequency sound generator 204 with a transmission circuit 114 radiates low-frequency sound to a subject 100 in order to stop or alleviate apnea and snoring by the stimulation of the low-frequency sound radiation. A low-frequency sound generator 204 with a transmission circuit 114 may radiate low-frequency sound to a subject 100 when a subject is hypopnea in order to stop or alleviate hypopnea.

Figure 5:
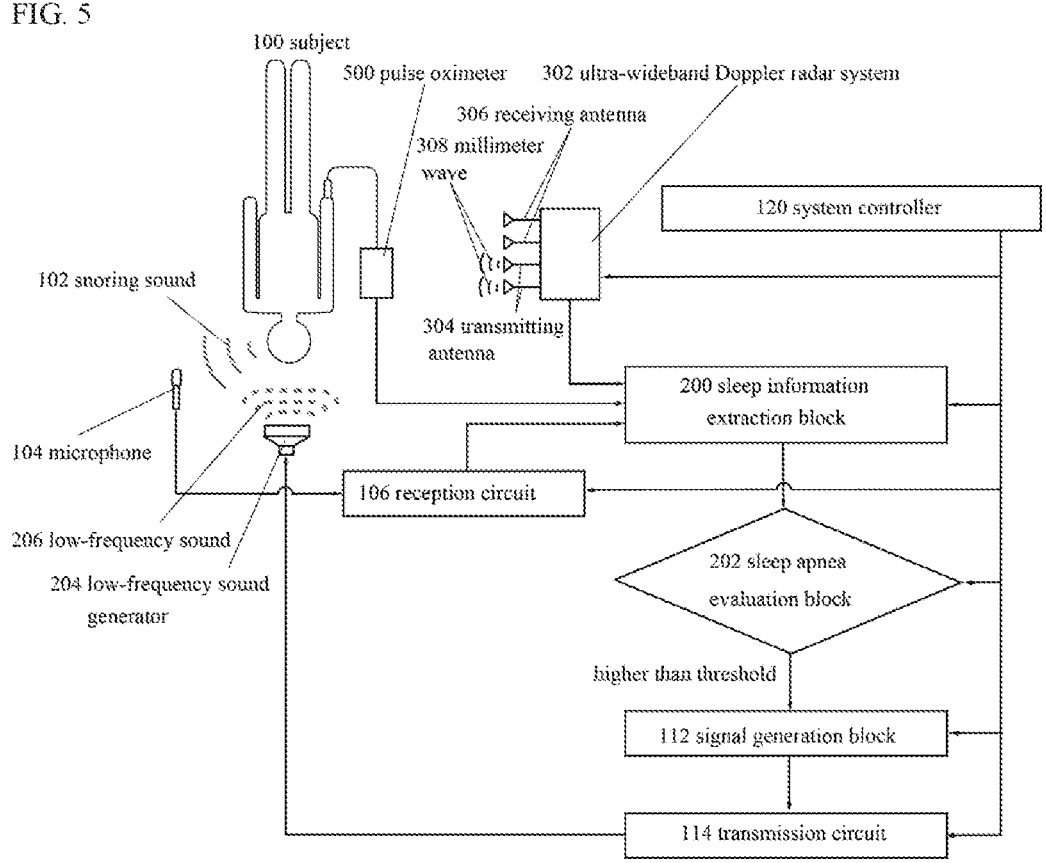
FIG. 5 is a schematic diagram of a sleep apnea treatment apparatus that radiates low-frequency sound to a subject when a subject becomes apnea or hypopnea during sleep, where an ultra-wideband Doppler radar system, a microphone and a pulse oximeter are employed to acquire breathing information.

A pulse oximeter 500 can be used. FIG. 5 shows a schematic diagram of a sleep apnea treatment apparatus employing an embodiment of the present invention. A pulse oximeter 500 acquires oxygen saturation information of a subject. In general, a pulse oximeter 500 acquires peripheral oxygen saturation ($SpO_2$) of a subject. Non-contact oxygen saturation monitor using one or plural cameras can be used to acquire oxygen saturation information, heartbeat information, and respiratory rate. A sleep information extraction block 200 extracts breathing information from a plurality of received signals acquired by an ultra-wideband Doppler radar system 302, a plurality of received sound signals acquired by a microphone 104 with a reception circuit, and $SpO_2$ information acquired by a pulse oximeter 500. A sleep apnea evaluation block 202 detects apnea, snoring and hypopnea of a subject. A pulse oximeter 500 can input SpO$_2$ information into a sleep apnea evaluand block 202 directly. When a sleep apnea evaluation block 202 detects apnea or hypopnea of a subject, a signal generation block 112 generates signals to produce low-frequency sound 206 using a low-frequency sound generator 204. A low-frequency sound generator 204 with a transmission circuit 114 radiates low-frequency sound to a subject 100 in order to stop or alleviate apnea and hypopnea by the stimulation of the low-frequency sound radiation. A low-frequency sound generator 204 with a transmission circuit 114 may radiate low-frequency sound to a subject 100 when a subject snores in order to stop or alleviate snoring.

The ultra-wideband Doppler radar system used in the present embodiment may transmits millimeter waves, where the center frequency of the millimeter waves is from 30 to 300 GHz, and the band width of the millimeter waves is 0.5 GHz or more.

A controller including circuitry may obtain breathing information and heart rate information from a plurality of received signals acquired by an ultra-wideband Doppler radar system, process the breathing information and heart rate information such that an index corresponding to breathing interruption, hypopnea, snoring, and/or precursor condition of apnea and hypopnea is determined based on the breathing information and heart rate information. The index is calculated from estimated heart rate, respiratory rate, and/or snoring sound.

A controller including circuitry may output sleep information. A sleep apnea treatment apparatus may radiate infrasound and/or audible sound to a subject. Infrasound is sound whose frequency is lower than 20 Hz. Audible sound is sound whose frequency is between 20 to 20,000 Hz.

A sleep apnea treatment apparatus may employ a low-frequency sound generator that radiates low-frequency sound to limited locations, including the locations at a subject head and/or other body part, selectively in order to suppress the impact of low-frequency sound radiation to a bed partner or people sleeping nearby the subject. Employment of at least two microphones or a radar system allows detection of the locations of the subject and the people sleeping nearby the subject based on interferometry.

Figure 6:
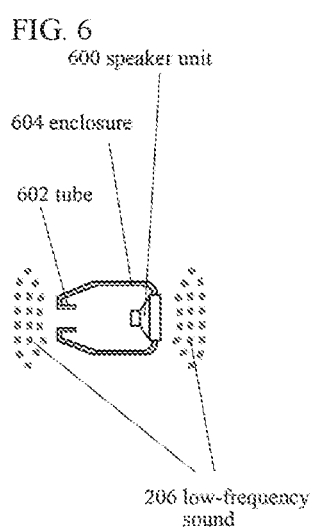
FIG. 6 is a schematic diagram showing a configuration of a sound-radiation device including a speaker unit, an enclosure, and a tube in order to radiate low-frequency sound to the near-field of the opening region of the tube and the near-field in front of the speaker unit.

A sound-radiation device using a speaker unit with an encloser and a tube may be used as a low-frequency that radiates low-frequency sound to the location at a subject selectively. FIG. 6 shows an arrangement of a sound-radiation device that may be used for an embodiment of the present invention. The sound-radiation device is provided with a speaker unit 600, an enclosure 604, and a tube (open-end tube portion) 602 in order to radiate low-frequency sound to the near-field of the opening region of the tube and the near-field in front of the speaker unit 600. The speaker unit 600 is placed on one open end of the enclosure, and the tube 602 is placed on another end of the enclosure 604 in the longitudinal direction. The size of the enclosure 604 may be larger than 10 cm in size. The opening location of a tube 602 is distant from the location of a speaker unit 600. A sound-radiation device of the present invention radiates low-frequency sound whose frequency is lower than the resonance frequency of the sound-radiation device. In this setting, the low-frequency sound radiated from the opening location of a tube 602 is almost antiphase to that radiated from a speaker unit 600. In general, the impact of low-frequency sound depends on the distance from a radiation point. In the near-field of the lateral region, the distance from a speaker unit $r_S$ and the distance from the opening location of a tube $r_T$ are almost same, that is, $r_S/r_T$ is close to 1. This means that the amplitude of low-frequency sound radiated from a speaker unit is close to the amplitude of low-frequency sound radiated from the opening location of a tube when the intensity of low-frequency sound radiated from a speaker unit is almost the same as the intensity of low-frequency sound radiated from the opening location of a tube. Therefore, the impact of low-frequency sound 206 in the near-field of the lateral region is suppressed because of the radiation of antiphase sound from a speaker unit 600 and the opening location of a tube 602. The impact of low-frequency sound 206 in the far-field is also suppressed because $r_S/r_T$ is close to 1. In contrast, in the near-field of the opening region of the tube and the near-field in front of the speaker unit, $r_S/r_T$ is far from 1. This means that the amplitude of low-frequency sound radiated from a speaker unit is far from the amplitude of low-frequency sound radiated from the opening location of a tube, that is, the low-frequency sound radiated from a speaker unit can not suppress the low-frequency sound radiated from the opening location of a tube effectively. Therefore, this setting enables to confine the impact of low-frequency sound 206 to the near-field of the opening region of the tube and the near-field in front of the speaker unit. The speaker unit includes at least one of a dynamic loudspeaker, a dynamic midrange speaker, and a dynamic tweeter.

Figure 7:
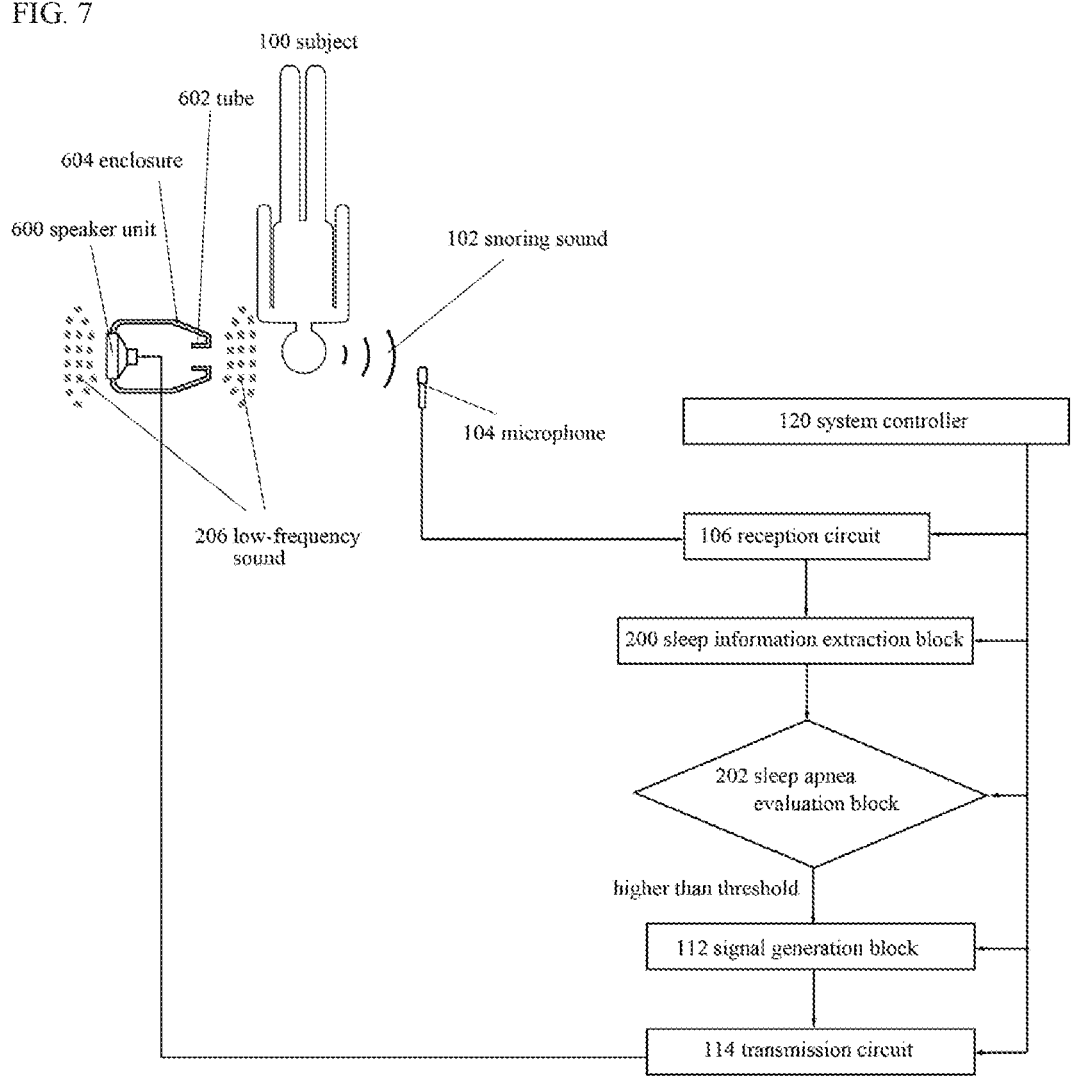
FIG. 7 is a schematic diagram of a sleep apnea treatment apparatus including a sound-radiation device that employs an enclosure, a tube and a speaker unit in order to radiate low-frequency sound.

FIG. 7 shows a schematic diagram of a sleep apnea treatment apparatus employing a sound-radiation device shown in FIG. 6. The apparatus is provided with one or plural microphones 104 with one or plural reception circuits 106 that convert a plurality of sounds produced by a subject to a plurality of received signals; a sleep information extraction block 200 that extracts breathing information from a plurality of received signals; a sleep apnea evaluation block 202 that evaluates breathing information and breathing interruption, snoring, and/or hypopnea of a subject; a signal generation block 112 that generates transmission signals in order to produce low-frequency sound 206 using a sound-radiation device; and a sound-radiation device with a transmission circuit 114, where the sound-radiation device is including a speaker unit, an enclosure, and a tube.

The frequency of the low-frequency sound radiated by the sound-radiation device is lower than the resonance frequency of the sound-radiation device, because in this setting the low-frequency sound radiated from the opening location of a tube 602 is almost antiphase to that radiated from a speaker unit 600.

The frequency of the low-frequency sound radiated by the sound-radiation device may be lower than one-third the resonance frequency of the sound-radiation device using the enclosure, because in this setting the frequency of the third harmonic of the low-frequency sound radiated by the sound radiation device is lower than the resonance frequency of the sound-radiation device, that is the third harmonic of the low-frequency sound radiated from the opening location of a tube 602 is also antiphase to that radiated from a speaker unit 600. The resonance frequency of the sound-radiation device mainly depends on the volume of the enclosure, the tube radius, and the tube length.

The frequency of the low-frequency sound radiated by the sound-radiation device may be from 20 to 100 Hz, and the resonance frequency of the sound-radiation device using the enclosure may be from 100 to 500 Hz, because in this setting the frequency of the fifth harmonic of the low-frequency sound radiated by the sound radiation device is also lower than the resonance frequency of the sound-radiation device.

The speaker unit or the opening region of the tube of a sound-radiation device used in the present invention may face to the subject, because the sound-radiation device radiates low-frequency sound to the near-field of the opening region of the tube and the near-field in front of the speaker unit.

Figure 8:
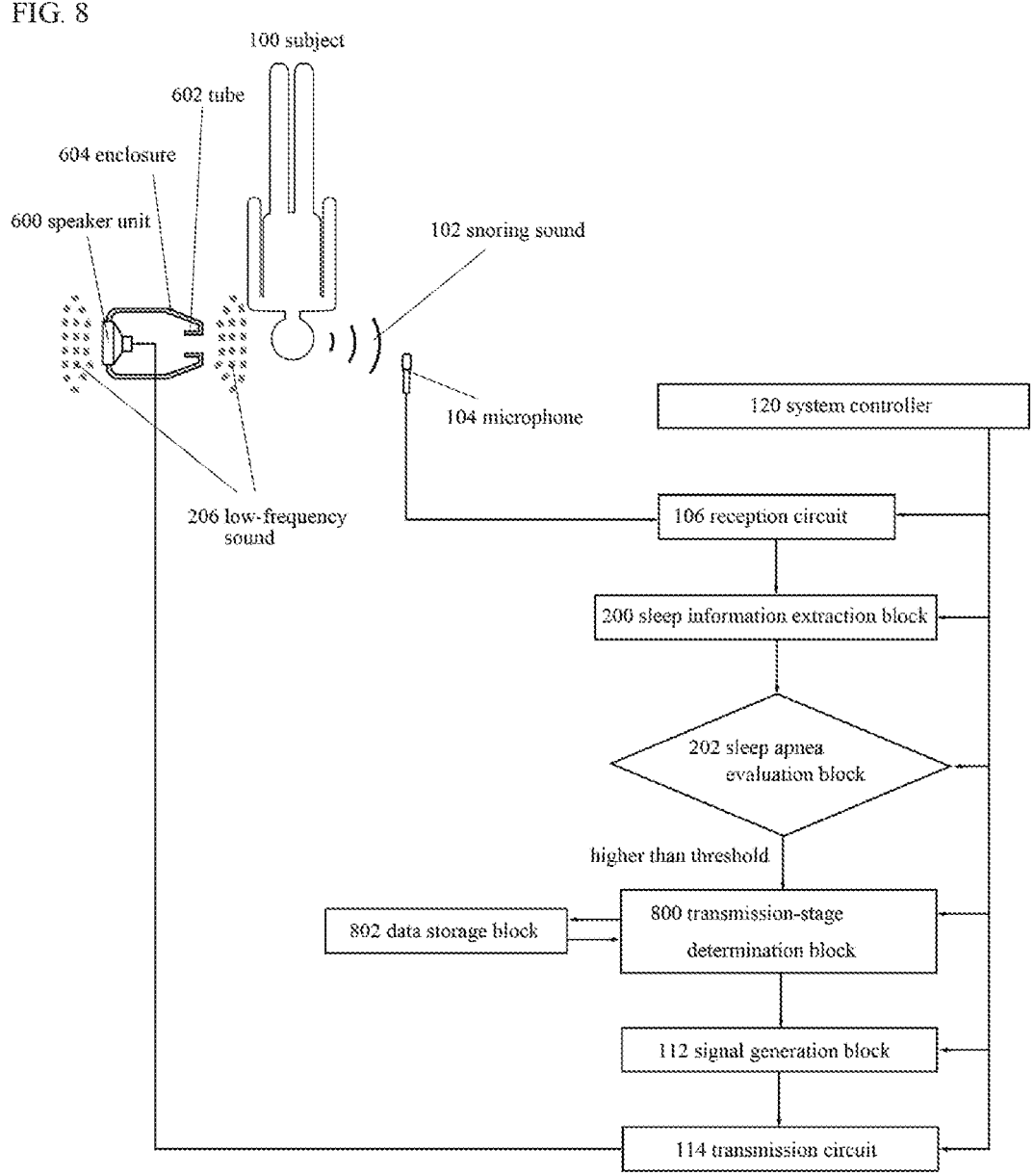
FIG. 8 is a schematic diagram of a sleep apnea treatment apparatus employing a data storage block.

A sleep apnea treatment apparatus may determine transmission signals using the data acquired and/or calculated by a sleep apnea evaluation block and/or a transmission-signal determination block. FIG. 8 shows a schematic diagram of a sleep apnea treatment apparatus employing a data storage block. The sleep apnea treatment apparatus is provided with one or plural microphones 104 with one or plural reception circuits 106 that convert a plurality of sounds produced by a subject to a plurality of received signals; a sleep information extraction block 200 that extracts breathing information from a plurality of received signals; a sleep apnea evaluation block 202 that evaluates breathing information and detects breathing interruption, snoring, and/or hypopnea of a subject; a transmission-stage determination block 800 that determines the stages of transmission; a data storage block 802 that stores data used and/or calculated by a sleep apnea evaluation block and/or a transmission-signal determination block; a signal generation block 112 that generates transmission signals in order to produce low-frequency sound using a low-frequency sound generator; and a low-frequency sound generator, including a speaker unit 600, a tube 602 and an enclosure 604, with a transmission circuit 114 that radiates low-frequency sound to a subject. The stages of transmission determine the types of transmission signals.

The frequency and/or intensity of transmission signal may increase when the low-frequency sound radiation to a subject failed to stop or alleviate apnea, hypopnea, and/or snoring of a subject during sleep in order to increase the impact of sound radiation to a subject.

The user can adjust the frequency and/or intensity of transmission signals directly. The frequency and/or intensity of transmission signals may be adjusted remotely based on the user condition, including medical condition.

A low-frequency sound may be radiated to a subject during silent or quiet term within each breathing, because the quiet environment is supposed to enforce the impact of low-frequency radiation. Low-frequency sounds may be radiated to a subject at exhalation phases, because in general snoring stops or decreases during exhalation phases.

The transmission-stage determination block may employ one or plural special stages from a certain time before wake-up time in order to wake a subject up comfortably. A certain time may be set from 30 to 60 minutes. Sound radiation may stop from a certain time before wake-up time in order to decrease the discomfort of a subject caused by unexpected waking-up. Low-intensity low-frequency sounds and/or music sounds may be radiated to a subject when the special stages are selected. Low-intensity low-frequency sounds and/or music sounds may be radiated intermittently. A sleep apnea treatment apparatus may apply vibration stimulation to a subject as the substitute of low-frequency sound radiation when the special stages are selected.

A sound-radiation device using a speaker may employ the condition that the distance between opening region of the tube and the location of the speaker unit is 10 cm or more, because a certain distance between opening region of the tube and the location of the speaker enables to confine the impact of low-frequency sound to the near-field of the opening region of the tube and the near-field in front of the speaker unit.

Figure 9:
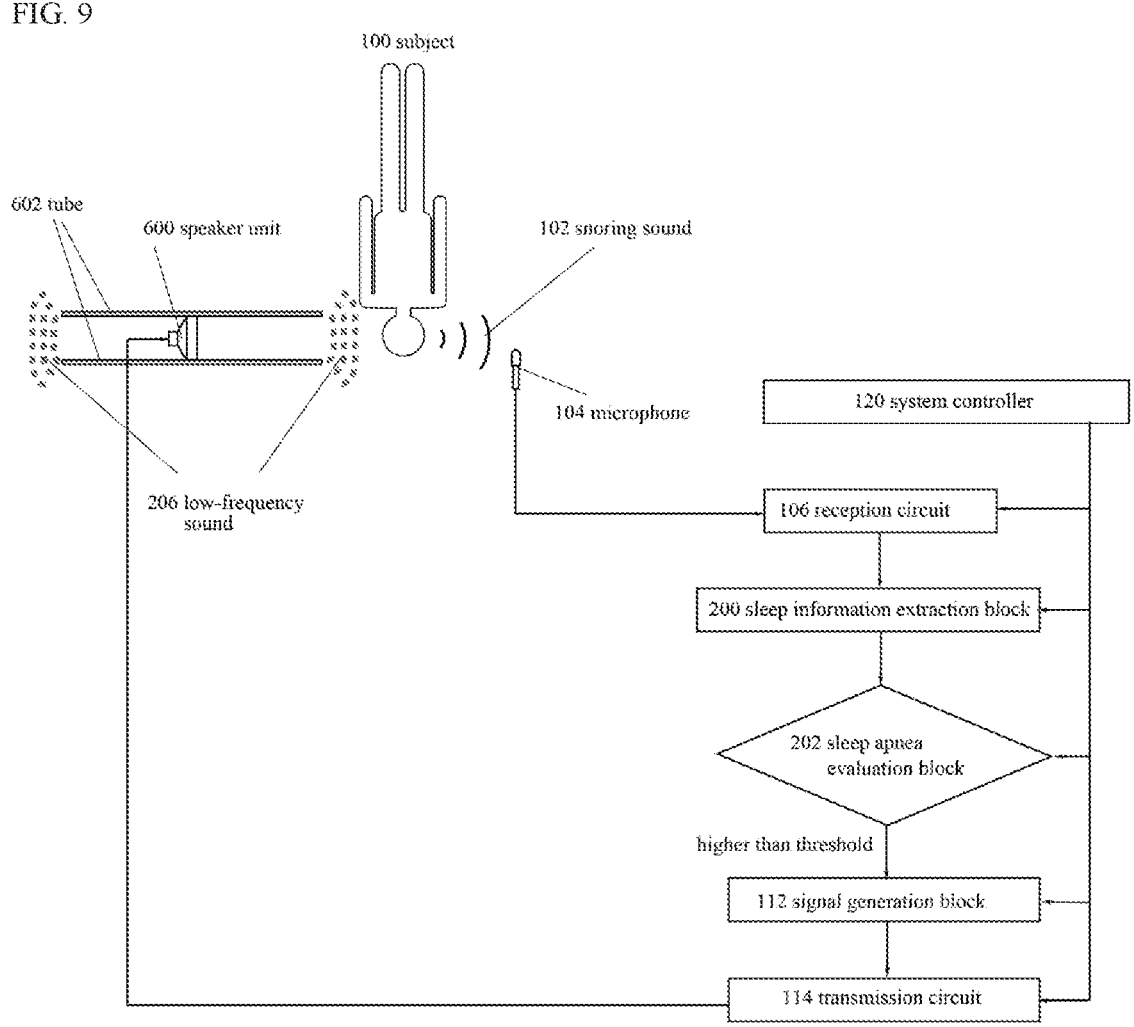
FIG. 9 is a schematic diagram of a sleep apnea treatment apparatus using a sound-radiation device that employs a tube and a speaker unit in order to radiate low-frequency sound.

A sound-radiation device using a speaker unit with a tube may be used as a low-frequency that radiates low-frequency sound to the location at a subject selectively. FIG. 9 shows a schematic diagram of a sleep apnea treatment apparatus employing a sound-radiation device using a speaker unit with a tube. A microphone 104 with a reception circuit 106 converts a plurality of sounds produced by a subject to a plurality of received signals. A microphone with a reception circuit in a cell phone is also applicable for the acquisition of a plurality of received signals. A sleep information extraction block 200 extracts breathing information from a plurality of received signals. A sleep apnea evaluation block 202 evaluates breathing information and detects breathing interruption, snoring, and/or hypopnea of a subject. A signal generation block 112 generates one or plural signals in order to radiate low-frequency sound 206 or audible sound using a tube 602 with a speaker unit 600. The low-frequency sound 206 or audible sound is applied to a subject 100 in order to stop or alleviate apnea, hypopnea, and/or snoring of a subject during sleep. The low-frequency sound radiated from one end of the tube 602 is almost antiphase to that from the other end of the tube 602. This setting enables to confine the impact of low-frequency sound 206 to the near-field of the opening region of the tube 602. The impact of low-frequency sound 206 in the near-field of the lateral region is suppressed because of the radiation of anti-phase sounds from the opposite end of the tube 602.

Both the tube ends of a sound-radiation device using a speaker with a tube face to a subject in order to radiate low-frequency sound to the location at a subject selectively.

Figure 10:
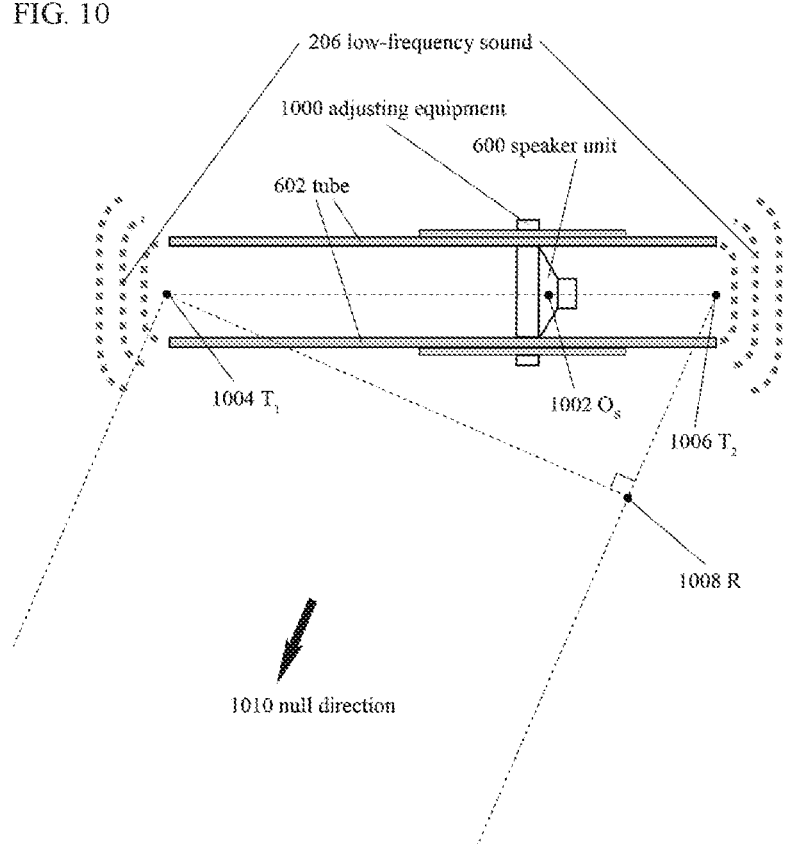
FIG. 10 is a schematic diagram showing a configuration of a sound-radiation device including a tube, a speaker unit, and an adjusting equipment that adjusts the position of the speaker unit.

The speaker unit of a sound-radiation device using a speaker unit with a tube may locate across the interior of the tube asymmetrically. A sound-radiation device using a speaker unit with a tube may employ an adjusting equipment 1000. FIG. 10 shows an arrangement of a sound-radiation device employing an embodiment of the presentation. An adjusting equipment (adjuster) 1000 adjusts the location of the speaker unit $O_S$ 1002 in the tube 602. Since the modification of the location of the speaker unit $O_S$ 1002 changes the phase difference between the low-frequency sound 206 at one end of the tube $T_1$ 1004 and the other end of the tube $T_2$ 1006, this modification can adjust the null direction 1010 of the radiation pattern of the low-frequency sound 206. In general, null direction 1010 satisfies the following conditions: $T_1O_S=O_ST_2+T_2R$ and the angle $T_1RT_2$ is a right angle. The null direction may be directed to a bed partner.

Figure 11:
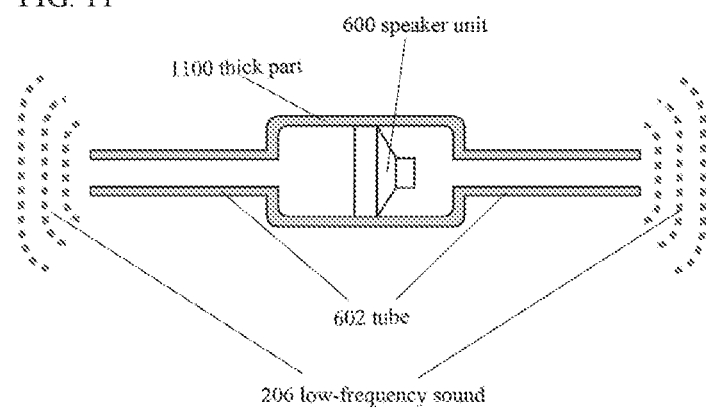
FIG. 11 is a schematic diagram showing a configuration of a sound-radiation device including a tube and a speaker unit that radiates low-frequency sound, where the tube has a thick part at the location of the speaker unit.

A tube with a thick part 1100 at the location of the speaker unit can be used. FIG. 11 shows the arrangement of the sound-radiation device employing an embodiment of the present invention. A thick part of the tube 1100 has a greater diameter and allows use of a large speaker unit 600 compared with the diameter of the distal region of the tube 602.

Figure 12:
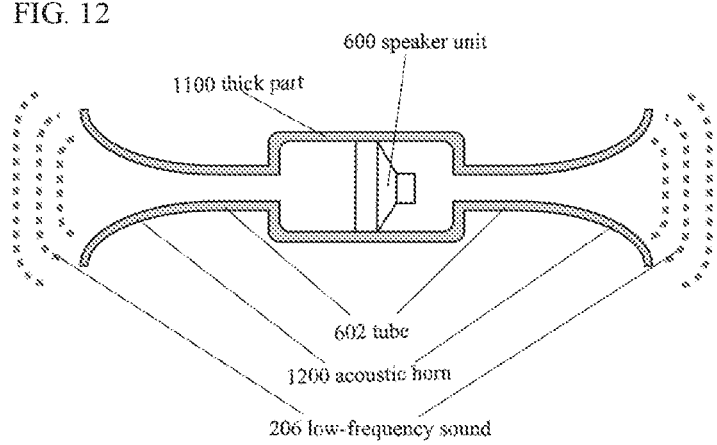
FIG. 12 is a schematic diagram showing a configuration of a sound-radiation device including a tube and a speaker unit that radiates low-frequency sound, where the both ends of the tube employ acoustic horns.

A tube with one or plural acoustic horns 1200 can be used. FIG. 12 shows the arrangement of the sound-radiation device employing an embodiment of the presentation. Acoustic horns 1200 are employed at the both ends of the tube 602. The apparatus may employ a thick part 1100 at the location of the speaker unit. Acoustic horns 1200 may be located in a thick part 1100 of the tube. Simple cone horn, exponential horn, multicell horn, radial horn, tractrix horn, constant directivity horn, mantaray horn, bi-radial horn, twin Bessel horn, constant directivity horn, multiple entry horn, and waveguide horn may be used as acoustic horns 1200.

Figure 13:
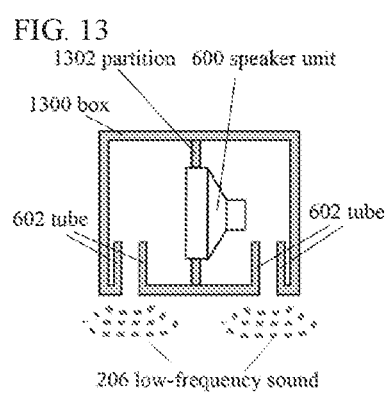
FIG. 13 is a schematic diagram showing a configuration of a sound-radiation device including a speaker unit that radiates low-frequency sound, a box with two parts which are divided by a partition, and two tubes.

A box 1300 with a partition 1302 can be used. FIG. 13 shows the arrangement of the sound-radiation device employing an embodiment of the present invention. A partition 1302 divides the interior of the box 1300 into two parts (two interior portions). A speaker unit 600 is located at the partition 1302 of the box 1300. The speaker unit 600 may be placed in or fitted to an opening of the partition 1302. Each of the two parts of the box communicates outside by one or plural tubes 602. Acoustic horns may be used as the substitute of tubes. The both opening directions of two tubes may direct to a subject 100.

Figure 14:
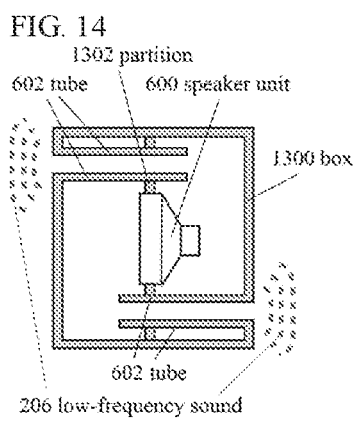
FIG. 14 is a schematic diagram showing a configuration of a sound-radiation device including a speaker unit that radiates low-frequency sound, a box with two parts which are divided by a partition, and two tubes, where each of the two tubes penetrates each part of the box.

A tube may penetrate a part of a box and communicate between outside and the other part of a box. FIG. 14 shows the arrangement of the sound-radiation device employing an embodiment of the presentation. This setting enables to employ long tubes. One or both the opening directions of two tubes may direct to a subject 100.

Figure 15:
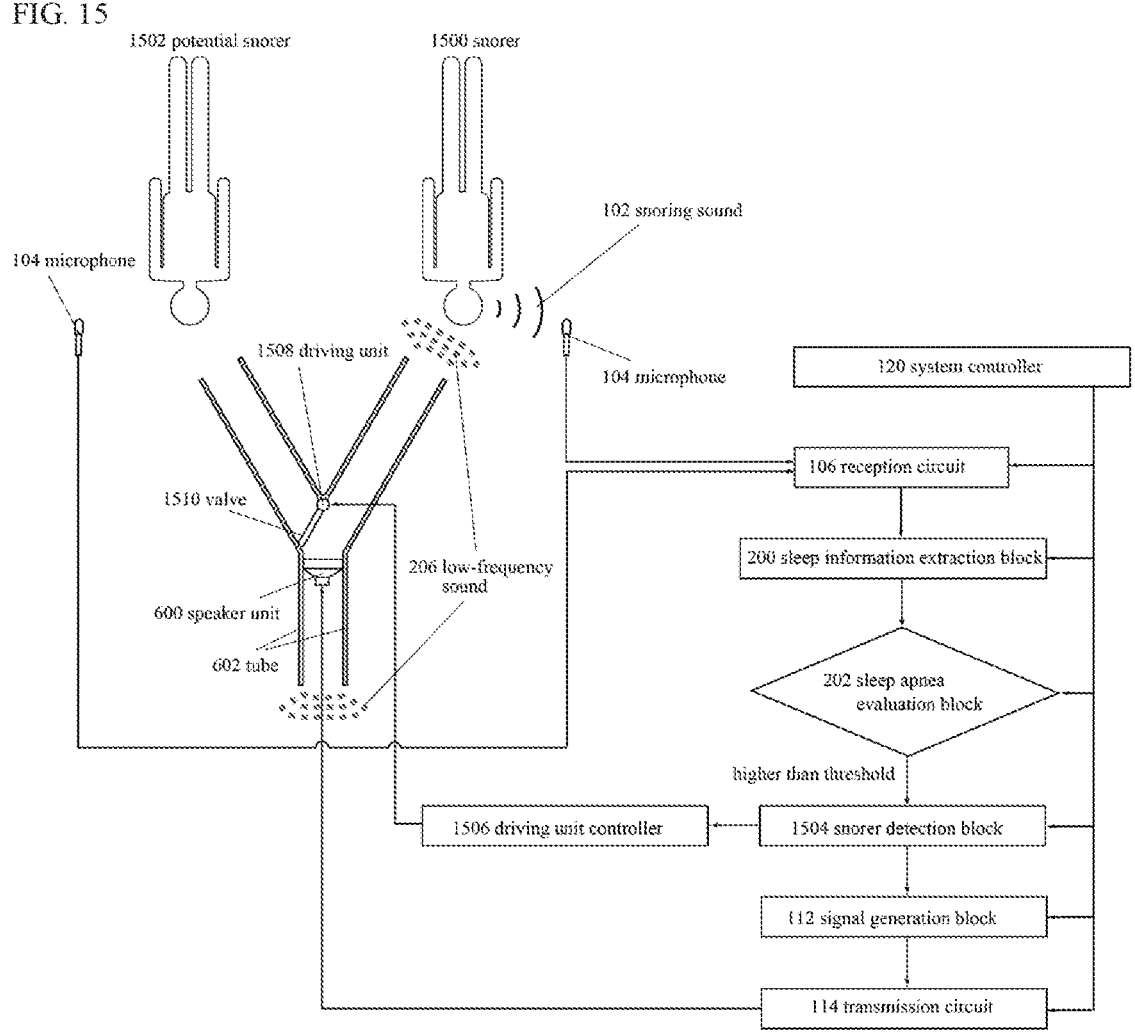
FIG. 15 is a schematic diagram of a sleep apnea treatment apparatus including a sound-radiation device that employs a speaker unit and a bifurcated tube with a valve, where the speaker unit locates across the interior of the tube, and the valve opens the branched tube that faces the direction of snorer.

A bifurcated tube with a valve can be used. FIG. 15 shows a schematic diagram of a sleep apnea treatment apparatus using a sound-radiation device that employs an embodiment of the present invention. Two or more microphones 104 with a reception circuit 106 convert a plurality of sounds produced by sleepers to a plurality of received signals. A microphone with a reception circuit in a cell phone is also applicable for the acquisition of a plurality of received signals. A sleep information extraction block 200 extracts breathing information from a plurality of received signals. A sleep apnea evaluation block 202 evaluates breathing information and detects breathing interruption, snoring, and/or hypopnea of a subject. A snorer detection block 1504 determines which is the snorer among sleepers using the received signals acquired by two or more microphones 104. A driving unit controller 1506 controls a driving unit 1508 in order to close one of the branched tubes by a valve 1510, where the open branched tube directs to the snorer 1500 estimated by the snorer detection block 1504. A driving unit controller 1506 can be implemented by at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read. A driving unit 1508 can be implemented by an actuator. Examples of actuators are solenoid, hydraulic cylinder, piezoelectric actuator, electric motor, and stepper motor. A signal generation block 112 generates one or plural signals in order to radiate low-frequency sound 206 or audible sound using a speaker unit 600 located across the interior of the tube. The low-frequency sound 206 or audible sound is applied to a snorer 1500 in order to stop or alleviate apnea, hypopnea, and/or snoring of a subject during sleep.

Figure 16:
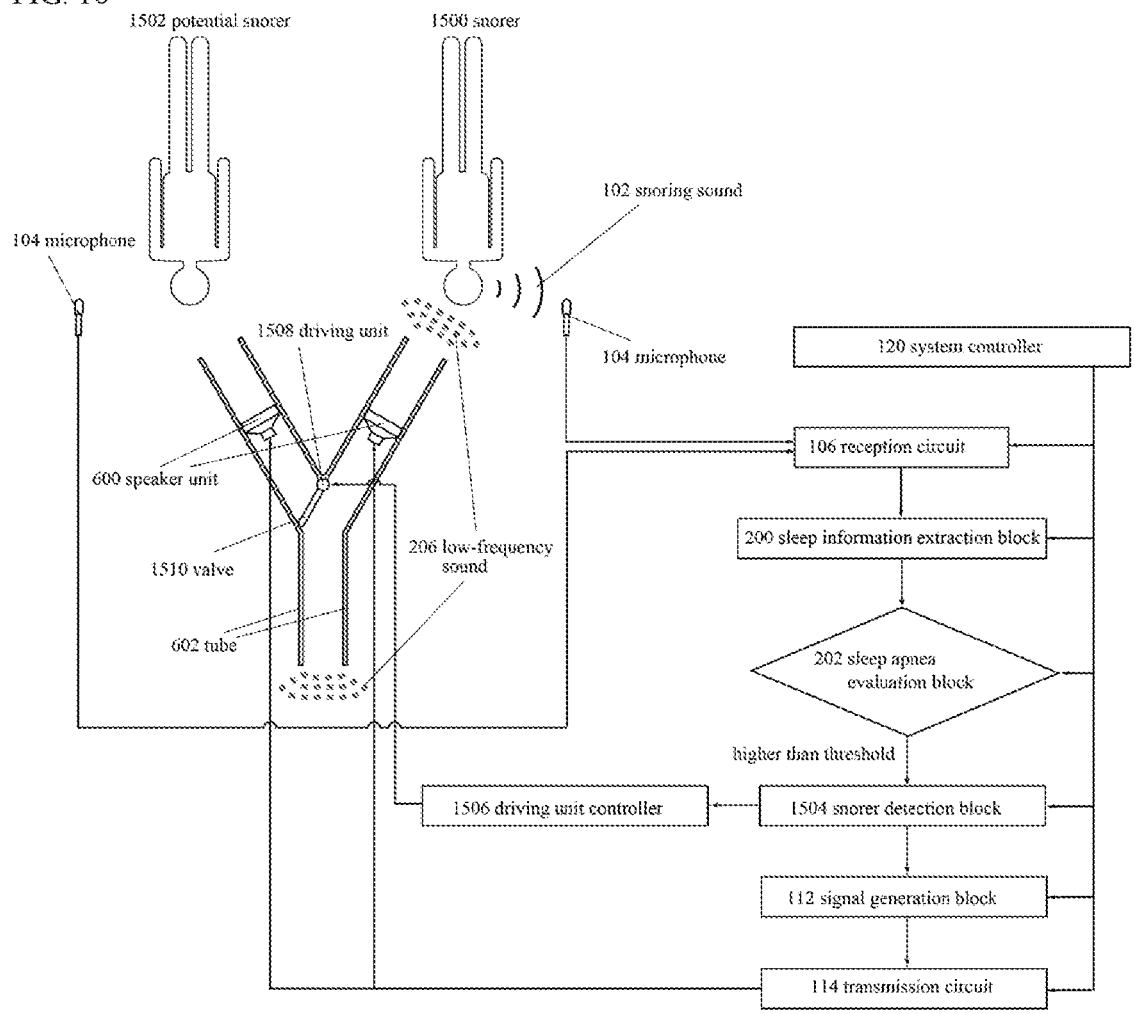
FIG. 16 is a sleep apnea treatment apparatus using a sound-radiation device that employs two speaker units; and a bifurcated tube, where each of the speaker unit locates across each of the branched tubes.

A bifurcated tube with two speaker units can be used. FIG. 16 shows a schematic diagram of a sleep apnea treatment apparatus using a sound-radiation device that employs an embodiment of the present invention. Two or more microphones 104 with a reception circuit 106 convert a plurality of sounds produced by sleepers to a plurality of received signals. A microphone with a reception circuit in a cell phone is also applicable for the acquisition of a plurality of received signals. A sleep information extraction block 200 extracts breathing information from a plurality of received signals. A sleep apnea evaluation block 202 evaluates breathing information and detects breathing interruption, snoring, and/or hypopnea of a subject. A snorer detection block 1504 determines which is the snorer among sleepers using the received signals acquired by two or more microphones 104. A driving unit controller 1506 controls a driving unit 1508 in order to close one of the branched tubes by a valve 1510, where the open branched tube directs to the snorer 1500 estimated by the snorer detection block 1504. Two speaker units 600 are located across the interior of the two branched tubes or at the end of the two branched tubes. A signal generation block 112 generates one or plural signals in order to radiate low-frequency sound 206 or audible sound using the speaker unit 600 that directs to a snorer 1500. The low-frequency sound 206 or audible sound is applied to a snorer 1500 in order to stop or alleviate apnea, hypopnea, and/or snoring of a subject during sleep. The speaker unit 600 that directs to a potential snorer 1502 may radiate low-frequency sound for cancellation in order to suppress the impact of the low-frequency sound radiated from the speaker unit 600 that directs to a snorer 1500. The sleep apnea treatment apparatus may exclude a valve with a driving unit and a driving unit controller.

Figure 17:
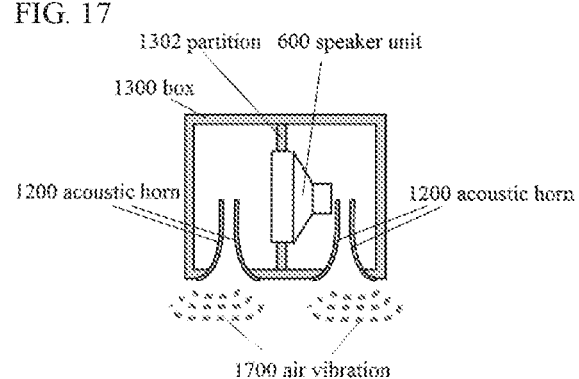
FIG. 17 is a schematic diagram showing a configuration of an air-vibration device including a speaker unit that generates air vibration.

A speaker unit may generate airflow or air-vibration in order to stimulate a snorer for the suppression of snoring. FIG. 17 shows the arrangement of the air-vibration device employing an embodiment of the present invention. A partition 1302 divides the interior of the box 1300 into two parts. A speaker unit 600 locates at the partition 1302 of the box 1300. Each of the two parts of the box communicates outside by one acoustic horn 1200. The both opening directions of two tubes direct to a snorer 1500. Air vibration is generated by the speaker unit 600 with a box 1300 and acoustic horns 1200. The air vibration 1700 generated from an acoustic horn 1200 is almost antiphase to that from the other acoustic horn 1200.

Another aspect of the present invention is a sleep apnea treatment method, including: converting a plurality of sounds produced by a subject to a plurality of received signals; obtaining breathing information from a plurality of received signals; processing the breathing information such that an index corresponding to breathing interruption, hypopnea, snoring, and/or precursor condition of apnea and hypopnea is determined based on the breathing information; and applying the low-frequency sound to the subject when the index is higher than a threshold.

First Exemplary Embodiment

FIG. 2 shows a schematic diagram of a sleep apnea treatment apparatus according to an embodiment of the present invention. The apparatus is provided with one or plural microphones 104 with one or plural reception circuits 106 that convert a plurality of sounds produced by a subject to a plurality of received signals; a sleep information extraction block 200 that extracts breathing information from a plurality of received signals; a sleep apnea evaluation block 202 that evaluates breathing information and detects breathing interruption, hypopnea, snoring, and/or precursor condition of apnea and hypopnea of a subject; a signal generation block 112 that generates signals in order to produce low-frequency sound 206 using a low-frequency sound generator 204; and a low-frequency sound generator 204 with a transmission circuit 114 that radiates low-frequency sound 206 to a subject 100.

Second Exemplary Embodiment

FIG. 5 shows a schematic diagram of a sleep apnea treatment apparatus according to an embodiment of the present invention. A pulse oximeter 500 acquires oxygen saturation information of a subject. In general, a pulse oximeter 500 acquires peripheral oxygen saturation ($SpO_2$)

of a subject. Non-contact oxygen saturation monitor using one or plural cameras can be used to acquire oxygen saturation information, heartbeat information, and respiratory rate. A sleep information extraction block 200 extracts breathing information from a plurality of received signals acquired by an ultra-wideband Doppler radar system 302, a plurality of received sound signals acquired by a microphone 104 with a reception circuit, and $SpO_2$ information acquired by a pulse oximeter 500. A sleep apnea evaluation block 202 detects apnea, snoring and hypopnea of a subject. A pulse oximeter 500 can input $SpO_2$ information into a sleep apnea evaluand block 202 directly. When a sleep apnea evaluation block 202 detects apnea or hypopnea of a subject, a signal generation block 112 generates signals to produce low-frequency sound 206 using a low-frequency sound generator 204. A low-frequency sound generator 204 with a transmission circuit 114 radiates low-frequency sound to a subject 100 in order to stop or alleviate apnea and hypopnea by the stimulation of the low-frequency sound radiation. A low-frequency sound generator 204 with a transmission circuit 114 may radiate low-frequency sound to a subject 100 when a subject snores in order to stop or alleviate snoring.

Third Exemplary Embodiment

FIG. 8 shows a schematic diagram of a sleep apnea treatment apparatus employing a data storage block. The sleep apnea treatment apparatus is provided with one or plural microphones 104 with one or plural reception circuits 106 that convert a plurality of sounds produced by a subject to a plurality of received signals; a sleep information extraction block 200 that extracts breathing information from a plurality of received signals; a sleep apnea evaluation block 202 that evaluates breathing information and detects breathing interruption, snoring, and/or hypopnea of a subject; a transmission-stage determination block 800 that determines the stages of transmission; a data storage block 802 that stores data used and/or calculated by a sleep apnea evaluation block and/or a transmission-signal determination block; a signal generation block 112 that generates transmission signals in order to produce low-frequency sound using a low-frequency sound generator; and a low-frequency sound generator, including a speaker unit 600, a tube 602 and an enclosure 604, with a transmission circuit 114 that radiates low-frequency sound to a subject. The stages of transmission determine the types of transmission signals.

The present invention has the following aspects.

1. Sleep apnea treatment apparatus that stimulates a subject when a subject snores includes: a stimulation device with a transmission circuit configured to apply stimulation to a subject; and a controller including circuitry configured to convert a plurality of sounds produced by a subject to a plurality of received signals, obtain snoring sound information from a plurality of received signals, process the snoring sound information such that an impact of snoring sound is determined based on the snoring sound information, and cause the stimulation device to apply stimulation to the subject when the impact is higher than a threshold.

2. Sleep apnea treatment apparatus that stimulates a subject when a subject becomes apnea, hypopnea and/or precursor condition of apnea and hypopnea during sleep, includes: a stimulation device with a transmission circuit configured to apply stimulation to a subject; and a controller including circuitry configured to convert a plurality of sounds produced by a subject to a plurality of received signals, obtain breathing information from a plurality of received signals, process the breathing information such that an index corresponding to breathing interruption, hypopnea, and/or precursor condition of apnea and hypopnea is determined based on the breathing information, and cause the stimulation device to apply stimulation to the subject when the index is higher than a threshold.

3. Sleep apnea treatment apparatus that radiates low-frequency sound to a subject when a subject becomes apnea, hypopnea and/or precursor condition of apnea and hypopnea during sleep includes: a low-frequency sound generator with a transmission circuit that radiates low-frequency sound to a subject; and a controller including circuitry configured to convert a plurality of sounds produced by a subject to a plurality of received signals, obtain breathing information from a plurality of received signals, process the breathing information such that an index corresponding to breathing interruption, hypopnea, snoring, and/or precursor condition of apnea and hypopnea is determined based on the breathing information, and cause the low-frequency sound generator to apply the low-frequency sound to the subject when the index is higher than a threshold.

4. Sleep apnea treatment apparatus that radiates low-frequency sound to a subject when a subject becomes apnea, hypopnea and/or precursor condition of apnea and hypopnea during sleep, includes: an ultra-wideband Doppler radar system that includes one or plural transmitting antennas and one or plural receiving antennas; a low-frequency sound generator with a transmission circuit that radiates low-frequency sound to a subject; and a controller including circuitry configured to obtain breathing information from a plurality of received signals acquired by an ultra-wideband Doppler radar system, process the breathing information such that an index corresponding to breathing interruption, hypopnea, snoring, and/or precursor condition of apnea and hypopnea is determined based on the breathing information, and cause the low-frequency sound generator to apply the low-frequency sound to the subject when the index is higher than a threshold.

5. Sleep apnea treatment apparatus that radiates low-frequency sound to a subject when a subject becomes apnea, hypopnea and/or precursor condition of apnea and hypopnea during sleep, includes: an ultra-wideband Doppler radar system that includes one or plural transmitting antennas and one or plural receiving antennas; a low-frequency sound generator with a transmission circuit that radiates low-frequency sound to a subject; and a controller including circuitry configured to convert a plurality of ultra-wideband electromagnetic waves reflected by a subject to a plurality of received radar signals using the ultra-wideband Doppler radar system, convert a plurality of sounds produced by a subject to a plurality of received sound signals, obtain breathing information from a plurality of received radar signals acquired by an ultra-wideband Doppler radar system and from a plurality of received sound signals, process the breathing information such that an index corresponding to breathing interruption, hypopnea, snoring, and/or precursor condition of apnea and hypopnea is determined based on the breathing information, and cause the low-frequency sound generator to apply the low-frequency sound to the subject when the index is higher than a threshold.

6. Sleep apnea treatment apparatus that radiates low-frequency sound to a subject when a subject becomes apnea, hypopnea and/or precursor condition of apnea and hypopnea during sleep, includes: an ultra-wideband Doppler radar system that includes one or plural transmitting antennas and one or plural receiving antennas; a pulse oximeter that acquires the $SpO_2$ information of a subject; a low-frequency sound generator with a transmission circuit that radiates low-frequency sound to a subject; and a controller including circuitry configured to convert a plurality of ultra-wideband electromagnetic waves reflected by a subject to a plurality of received radar signals using the ultra-wideband Doppler radar system, convert a plurality of sounds produced by a subject to a plurality of received sound signals, obtain breathing information from a plurality of received radar signals acquired by an ultra-wideband Doppler radar system, from the $SpO_2$ information of a subject, and from a plurality of received sound signals, process the breathing information such that an index corresponding to breathing interruption, hypopnea, snoring, and/or precursor condition of apnea and hypopnea is determined based on the breathing information, and cause the low-frequency sound generator to apply the low-frequency sound to the subject when the index is higher than a threshold.

7. Sleep apnea treatment apparatus according to 4, wherein an ultra-wideband Doppler radar system transmits millimeter waves; the center frequency of the millimeter waves is from 30 to 300 GHz, and the band width of the millimeter waves is 0.5 GHz or more.

8. Sleep apnea treatment apparatus according to 4, wherein a controller including circuitry configured to obtain breathing information and heart rate information from a plurality of received signals acquired by an ultra-wideband Doppler radar system, process the breathing information and heart rate information such that an index corresponding to breathing interruption, hypopnea, snoring, and/or precursor condition of apnea and hypopnea is determined based on the breathing information and heart rate information, and cause the low-frequency sound generator to apply the low-frequency sound to the subject when the index is higher than a threshold.

9. Sleep apnea treatment apparatus according to 1, 2, 3, 4, 5 and 6, wherein a controller including circuitry outputs sleep information.

10. Sleep apnea treatment apparatus according to 3, 4, 5 and 6, wherein a sleep apnea treatment apparatus radiates infrasound and/or audible sound to a subject.

11. Sleep apnea treatment apparatus according to 3, 4, 5 and 6, wherein a low-frequency sound generator radiates low-frequency sound to limited locations selectively.

12. Sound-radiation device using a speaker unit that radiates low-frequency sound to limited locations includes: a speaker unit that radiates low-frequency sound; an enclosure; and a tube; the opening region of the tube and the location of the speaker unit is distant, and the speaker unit includes a dynamic loudspeaker, a dynamic midrange speaker, and a dynamic tweeter.

13. Sleep apnea treatment apparatus according to 3, 4, 5 and 6, wherein a sound-radiation device using a speaker unit according to 12 is employed as a low-frequency sound generator.

14. Sound-radiation device according to 12, wherein the frequency of the low-frequency sound radiated by the sound-radiation device is lower than the resonance frequency of the sound-radiation device.

15. Sound-radiation device according to 12, wherein the frequency of the low-frequency sound radiated by the sound-radiation device is lower than one-third the resonance frequency of the sound-radiation device.

16. Sound-radiation device according to 12, wherein the frequency of the low-frequency sound radiated by the sound-radiation device is from 20 to 100 Hz, and the resonance frequency of the sound-radiation device is from 100 to 500 Hz.

17. Sound-radiation device according to 12, wherein the speaker unit or the opening region of the tube face to the subject.

18. Sleep apnea treatment apparatus according to 3, 4, 5 and 6, wherein the controller including circuitry configured to convert a plurality of sounds produced by a subject to a plurality of received signals, obtain breathing information from a plurality of received signals, process the breathing information such that an index corresponding to breathing interruption, hypopnea, snoring, and/or precursor condition of apnea and hypopnea is determined based on the breathing information, determine the stage of transmission based on the index, store data used and/or calculated by the controller, and cause the low-frequency sound generator to apply the low-frequency sound to the subject based on the stage of transmission.

19. Sleep apnea treatment apparatus according to 3, 4, 5 and 6, wherein the frequency and/or intensity of transmission signals increase when the low-frequency sound radiation to a subject failed to stop or alleviate apnea, hypopnea, and/or snoring of a subject during sleep.

20. Sleep apnea treatment apparatus according to 3, 4, 5 and 6, wherein the frequency and/or intensity of transmission signals can be adjusted directly and/or remotely.

21. Sleep apnea treatment apparatus according to 3, 4, 5 and 6, wherein low-frequency sound is radiated to a subject during silent or quiet term within each breathing.

22. Sleep apnea treatment apparatus according to 3, 4, 5 and 6, wherein low-frequency sounds are radiated to a subject at exhalation phases.

23. Sleep apnea treatment apparatus according to 18, wherein the controller including circuitry further configured to determine one of plural special stages as the stage of transmission from a certain time before wake-up time.

24. Sleep apnea treatment apparatus according to 23, wherein no radiation, low-intensity low-frequency sound radiation and/or music sound radiation are selected when the stage of transmission is one of the special stages.

25. Sleep apnea treatment apparatus according to 24, wherein low-intensity low-frequency sounds and/or music sounds are radiated intermittently.

26. Sleep apnea treatment apparatus according to 23, wherein the sleep apnea treatment apparatus applies vibration stimulation to a subject as the substitute of low-frequency sound radiation when the special stages are selected.

27. Sound-radiation device using a speaker unit according to 12, wherein the distance between opening region of the tube and the location of the speaker unit is 10 cm or more.

28. Sound-radiation device using a speaker unit that radiates low-frequency sound, includes: a speaker unit that radiates low-frequency sound; and a tube through which low-frequency sound transmits; the speaker unit locates across the interior of the tube.

29. Sound-radiation device using a speaker unit that radiates low-frequency sound to limited locations according to 28, wherein both the tube ends face to a subject.

30. Sound-radiation device according to 28, wherein the speaker unit locates across the interior of the tube asymmetrically.

31. Sound-radiation device according to 28, further includes: an adjusting equipment that adjusts the location of the speaker unit in the tube.

32. Sound-radiation apparatus according to 28, wherein the tube has a thick part at the location of the speaker unit.

33. Sound-radiation apparatus according to 28 and 32, wherein the both ends of the tube employ acoustic horns; the acoustic horn includes simple cone horn, exponential horn, multicell horn, radial horn, tractrix horn, constant directivity horn, mantaray horn, bi-radial horn, twin Bessel horn, constant directivity horn, multiple entry horn, and waveguide horn.

34. Sound-radiation device using a speaker unit that radiates low-frequency sound, includes: a speaker unit that radiates low-frequency sound; a box with two parts which are divided by a partition; and two tubes; the speaker unit locates at the partition of the box, and each of the two parts of the box communicates outside by one or plural tubes.

35. Sound-radiation device according to 34, wherein each of the tubes penetrates the other part of the box.

36. Sound-radiation device using a speaker unit that radiates low-frequency sound, includes: a speaker unit that radiates low-frequency sound; and a bifurcated tube with a valve; the speaker unit locates across the interior of the tube, the valve closes one of the branched tubes, and the valve opens the branched tube that faces the direction of snoring sound.

37. Sound-radiation device using a speaker unit that radiates low-frequency sound, includes: two speaker units that radiates low-frequency sound; and a bifurcated tube; each of the speaker unit locates across each of the branched tubes or at the end of each branched tube.

38. Air-vibration device using a speaker unit that generates air vibration includes: a speaker unit that generates air vibration; a box with two parts which are divided by a partition; and two acoustic horns or two tubes through which air-vibration transmits; the speaker unit locates at the partition of the box, and each of the two parts of the box communicates outside by one or plural acoustic horns or tubes.

39. Anti-snoring apparatus according to 1, 2, 3, 4, 5 and 6.

40. Sleep apnea treatment method, including: converting a plurality of sounds produced by a subject to a plurality of received signals; obtaining breathing information from a plurality of received signals; processing the breathing information such that an index corresponding to breathing interruption, hypopnea, snoring, and/or precursor condition of apnea and hypopnea is determined based on the breathing information; and applying the low-frequency sound to the subject when the index is higher than a threshold.

Sleep apnea treatment apparatus in one aspect of the present invention is an apparatus that radiates low-frequency sound to a subject when a subject becomes apnea, hypopnea and/or precursor condition of apnea and hypopnea during sleep, including: a low-frequency sound generator with a transmission circuit that radiates low-frequency sound to a subject; and a controller including circuitry configured to convert a plurality of sounds produced by a subject to a plurality of received signals, obtain breathing information from a plurality of received signals, process the breathing information such that an index corresponding to breathing interruption, hypopnea, snoring, and/or precursor condition of apnea and hypopnea is determined based on the breathing information, and cause the low-frequency sound generator to apply the low-frequency sound to the subject when the index is higher than a threshold.

Another aspect of the present invention is a sleep apnea treatment method including: converting a plurality of sounds produced by a subject to a plurality of received signals; obtaining breathing information from a plurality of received signals; processing the breathing information such that an index corresponding to breathing interruption, hypopnea, snoring, and/or precursor condition of apnea and hypopnea is determined based on the breathing information; and applying the low-frequency sound to the subject when the index is higher than a threshold.

REFERENCE SIGNS LIST 100 subject
102 snoring sound
104 microphone
106 reception circuit
108 snoring sound extraction block
110 snoring sound evaluation block
112 signal generation block
114 transmission circuit
116 stimulation device
118 stimulation
120 system controller
200 sleep information extraction block
202 sleep apnea evaluation block
204 low-frequency sound generator
206 low-frequency sound
302 ultra-wideband Doppler radar system
304 transmitting antenna
306 receiving antenna
308 millimeter wave
500 pulse oximeter
600 speaker unit
602 tube
604 enclosure
800 transmission-stage determination block
802 data storage block
1000 adjusting equipment
1002 $O_S$
1004 $T_1$
1006 $T_2$
1008 R
1010 null direction
1100 thick part
1200 acoustic horn
1300 box
1302 partition
1500 snorer
1502 potential snorer
1504 snorer detection block
1506 driving unit controller
1508 driving unit
1510 valve
1700 air vibration

What is claimed is:
1. A sleep apnea treatment apparatus, comprising:
a stimulation device configured to apply a stimulation to a subject; and
a controller comprising circuitry configured to receive a plurality of sounds produced by the subject, convert the plurality of sounds to a plurality of received sound signals, obtain breathing information from the plurality of received sound signals, calculate an index corresponding to breathing interruption, hypopnea, and/or precursor condition of apnea and hypopnea based on the breathing information, and cause the stimulation device to apply the stimulation to the subject when the index is higher than a threshold,
wherein the stimulation device comprises a low-frequency sound generator, and the stimulation comprises a low-frequency sound, and wherein the circuitry is further configured to apply the low-frequency sound to the subject at an exhalation phase.

2. The sleep apnea treatment apparatus according to claim 1, further comprising:
an ultra-wideband Doppler radar system which includes at least one transmitting antenna and at least one receiving antenna and is configured to transmit a plurality of ultra-wideband electromagnetic waves to the subject and receive the plurality of ultra-wideband electromagnetic waves reflected by the subject,
wherein the circuitry is configured to convert the plurality of ultra-wideband electromagnetic waves received by the ultra-wideband Doppler radar system to a plurality of received radar signals, convert the plurality of sounds produced by the subject to the plurality of received sound signals, obtain breathing information from the plurality of received radar signals and from the plurality of received sound signals, calculate the index corresponding to breathing interruption, hypopnea, snoring, and/or precursor condition of apnea and hypopnea based on the breathing information, and cause the low frequency sound generator to apply the low-frequency sound to the subject when the index is higher than the threshold.

3. The sleep apnea treatment apparatus according to claim 2, wherein the ultra-wideband Doppler radar system is configured to transmit millimeter waves having a center frequency of from 30 to 300 GHz and a band width of 0.5 GHz or more.

4. The sleep apnea treatment apparatus according to claim 2, wherein the circuitry is further configured to obtain heart rate information from the plurality of received radar signals and calculate the index based on the breathing information and the heart rate information.

5. The sleep apnea treatment apparatus according to claim 4, wherein the circuitry is further configured to output sleep information.

6. The sleep apnea treatment apparatus according to claim 1, further comprising: a pulse oximeter configured to acquire $SpO_2$ information of the subject, wherein the circuitry is configured to obtain breathing information from the plurality of received radar signals, from the $SpO_2$ information, and from the plurality of received sound signals.

7. The sleep apnea treatment apparatus according to claim 1, wherein the circuitry is further configured to determine a stage of treatment based on the index, store data used and/or calculated by the controller, and cause the low-frequency sound generator to apply the low-frequency sound to the subject based on the stage of treatment.

8. The sleep apnea treatment apparatus according to claim 7, wherein the circuitry is further configured to determine at least one special stage as a stage of transmission from a certain time before wake-up time.

9. The sleep apnea treatment apparatus according to claim 8, wherein no radiation, low-intensity low-frequency sound radiation and/or music sound radiation are selected when the stage of transmission is one of the at least one special stage.

10. The sleep apnea treatment apparatus according to claim 8, wherein the sleep apnea treatment apparatus is configured to apply applies vibration stimulation to the subject as a substitute of low frequency sound radiation when the at least one special stages are is selected.

11. The sleep apnea treatment apparatus according to claim 7, wherein the low-frequency sound generator is configured to apply the low-frequency sound intermittently.

12. The sleep apnea treatment apparatus according to claim 1, wherein the circuitry is further configured to increase frequency and/or intensity of the low-frequency sound when radiation of the low-frequency sound to the subject failed to stop or alleviate apnea, hypopnea, and/or snoring of the subject during sleep.

13. The sleep apnea treatment apparatus according to claim 1, wherein the circuitry is further configured to adjust frequency and/or intensity of the low-frequency sound.

14. The sleep apnea treatment apparatus according to claim 1, wherein the circuitry is further configured to apply the low-frequency sound to the subject during a silent or quiet term within breathing.

\* \* \* \* \*